United States Patent
Joshi

(10) Patent No.: US 10,105,462 B2
(45) Date of Patent: Oct. 23, 2018

(54) AIR FRESHENER WITH OPTIONAL DRAIN CLEANER

(71) Applicant: Microlin, LLC, Salt Lake City, UT (US)

(72) Inventor: Ashok V. Joshi, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 342 days.

(21) Appl. No.: 14/792,332

(22) Filed: Jul. 6, 2015

(65) Prior Publication Data

US 2017/0007734 A1    Jan. 12, 2017

(51) Int. Cl.
*A61L 9/01* (2006.01)
*A61L 9/04* (2006.01)
*A61L 9/12* (2006.01)

(52) U.S. Cl.
CPC ............. *A61L 9/01* (2013.01); *A61L 9/042* (2013.01); *A61L 9/127* (2013.01)

(58) Field of Classification Search
CPC ... A61L 9/01; A61L 9/042; A61L 9/12; A61L 9/127
See application file for complete search history.

(56) References Cited

U.S. PATENT DOCUMENTS

| | | | |
|---|---|---|---|
| 5,139,864 A | 8/1992 | Lindauer | |
| 5,336,424 A | 8/1994 | Van Vlahakis et al. | |
| 5,813,058 A | 9/1998 | Quigley et al. | |
| 8,007,707 B1 | 8/2011 | Brown et al. | |
| 2004/0037792 A1 | 2/2004 | Hiramoto et al. | |
| 2005/0148479 A1 | 7/2005 | Barthel et al. | |
| 2013/0031708 A1 | 2/2013 | Sensel | |
| 2014/0075663 A1 | 3/2014 | Irwin et al. | |
| 2014/0259344 A1 | 9/2014 | Muderlak et al. | |
| 2015/0069088 A1 | 3/2015 | Olson et al. | |

OTHER PUBLICATIONS

International Search Report and Written Opinion of the International Searching Authority, PCT/US16/41007, dated Sep. 16, 2016.

*Primary Examiner* — Tuan N Nguyen
(74) *Attorney, Agent, or Firm* — Brian Trask

(57) ABSTRACT

An automatic air freshener that operates for a period of time in excess of about 14 days, and that may optionally include a drain cleaner, mosquito repellant, or other beneficial fluid. Certain embodiments are adapted for disposal in a urinal, although a variety of other applications are contemplated. An air freshener may operate by: emanation of scent from a rubber or rubber-like material that carries a dispersed scented oil; gravity-induced drip from a bulk supply of scented fluid through a small orifice; osmotic transfer of scented fluid from a bulk supply; or gas-pump drive of scented fluid at controlled pressure. When present, the drain cleaner typically is carried by a container structured to permit a slow drip of drain cleaning fluid from a bulk fluid supply.

20 Claims, 8 Drawing Sheets

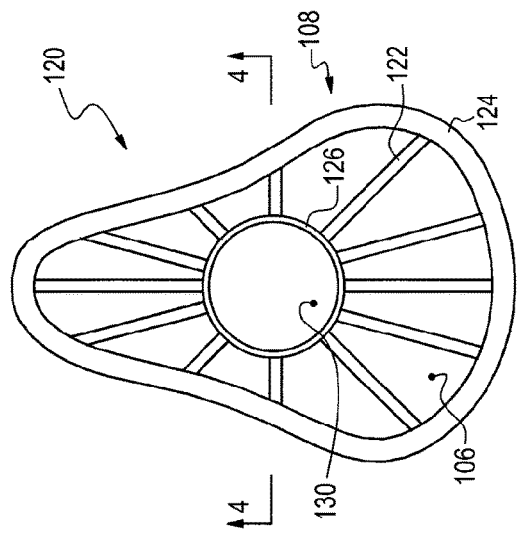
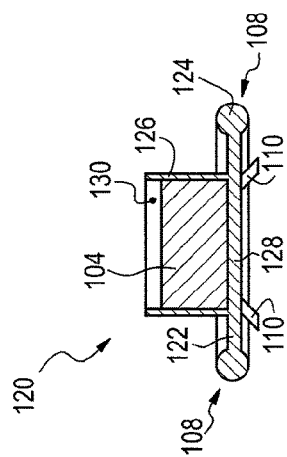
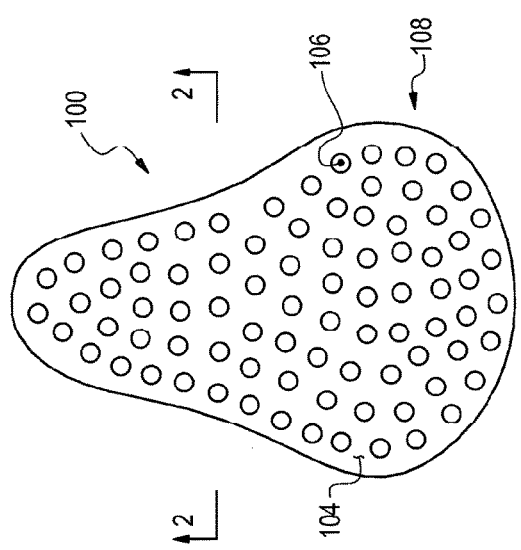
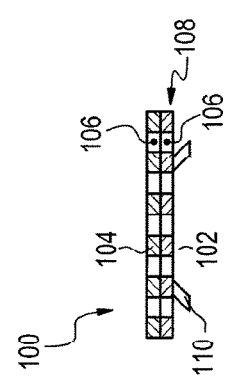

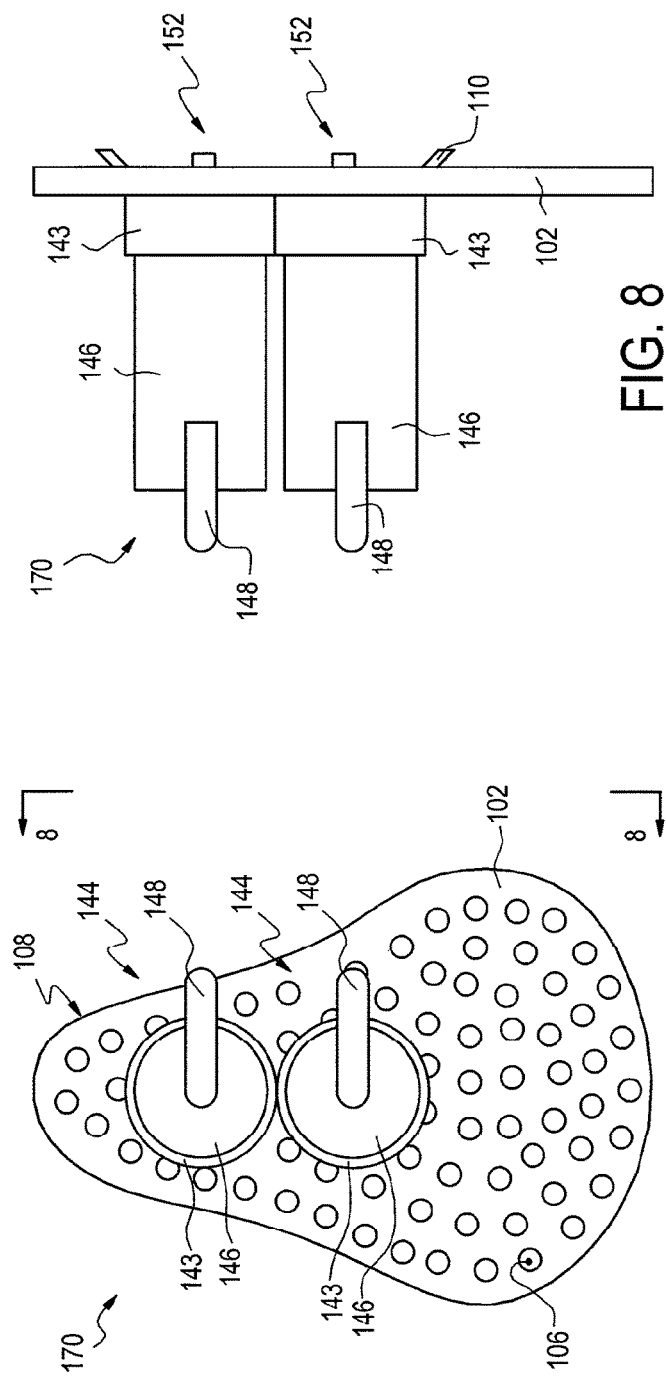
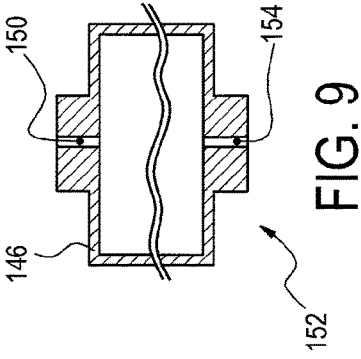

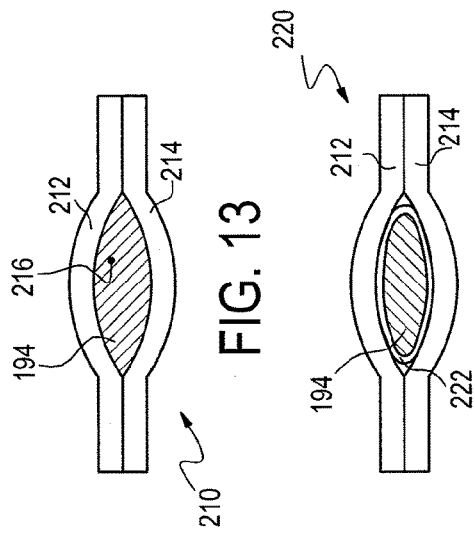
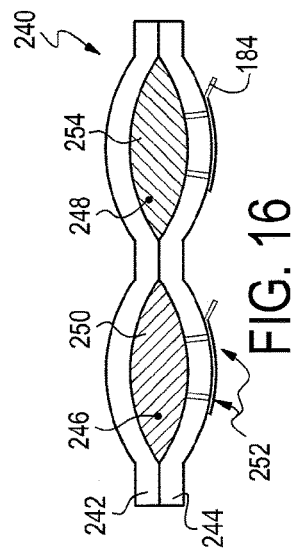
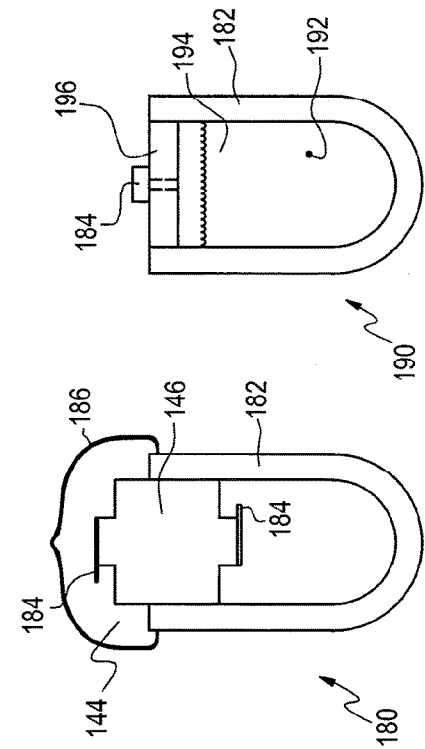
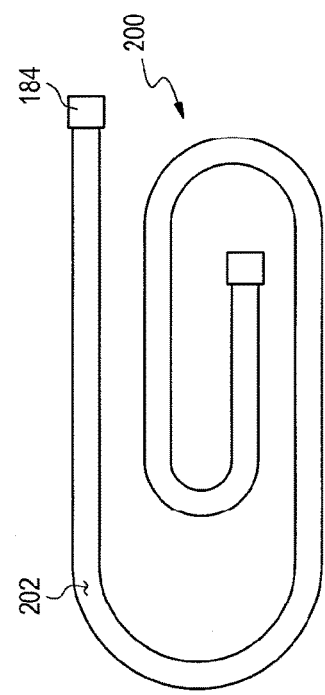

AIR FRESHENER WITH OPTIONAL DRAIN CLEANER

BACKGROUND

Field of the Invention:

This invention relates generally to products for air freshening and/or drain cleaning, and their use.

State of the Art:

Air freshening, and/or masking of unpleasant odors, is commonly done in certain enclosed environments, such as bathrooms and automobiles. A typical air treatment includes introduction of a masking fragrance, or scent, into the environment. Known devices for introducing a scent or fragrance into the environment on-demand include aerosols, which may be hand operated when a need is detected.

Some devices may automatically dose the environment over a desirable period of time. Certain such devices require an additional source of energy, such as devices that are plugged into an electrical outlet to operate a warming element. Other devices are structured to off-gas, or sublimate, under the ambient conditions of the environment in which they are deployed. One such device includes a puck of mothball-like material that can be placed into a urinal. Another air freshener includes a fragrance-soaked ornament that is structured to hang on a rear view mirror of an automobile. Typically, such a device produces an initially strong fragrance that steadily diminishes over time.

Introduction of scent may also be performed during certain processing operations, such as when drying articles of clothing in a mechanical clothes drier. For example, it is known to include scent as a dry component carried on a disposable sheet of substrate that also is structured to reduce build-up of static electricity.

It would be an improvement to provide an air freshening material and device that can dispense scent to an environment automatically over a period of time in excess of about 14 days without requiring an additional energy source, and optionally provide an additional function, such as drain cleaning. Desirably, the improved air-freshening device will produce a substantially constant level of detectable fragrance in the environment over the desired time increment.

BRIEF SUMMARY OF THE INVENTION

Certain embodiments structured according to principles of this invention typically provide an automatic air freshener for use over a period of time in excess of about 14 days. A preferred embodiment includes a first container and an air freshener disposed in association with the first container. In some cases, the air freshener includes a material selected from the group consisting of (styrene-based polymers, styrene-based rubbers, EPDM, gum rubber, and cellulosic rubber); and a scented fluid dispersed into the material to a weight percent of between about 20% and about 200%, where weight percent is calculated as A/B*100, and A is weight of scented fluid and B is weight of material. An operable scented fluid is a scent-emitting oil.

A workable emanator may be formed by causing scented fluid to be dispersed into the styrene-based material to a weight percent of greater than about 30%. An emanator may include a scented fluid that is dispersed into styrene-based material to a weight percent of between about 30% and about 150%, or more.

An emanator operable in certain embodiments may be made from a styrene-based polymer or a styrene-based rubber. Workable styrene-based polymers include acrylonitrile-butadiene-styrene (ABS), styrene-butadiene-styrene (SBS), styrene-acrylonitrile (SAN), styrene-isoprene-styrene (SIS), styrene-ethylene-butadiene-styrene (SEBS), styrene-ethylene-propylene-styrene (SEPS), and combinations thereof. A workable styrene-based rubber includes styrene-butadiene-rubber.

A portion of the first container can be formed from scent-bearing styrene-based material. Alternatively, the air freshener can be disposed inside of, or even carried on, the first container. Sometimes, an excess quantity of scented fluid is carried inside the first container, and the first container functions as an emanator to discharge scent into the environment. In one preferred type of embodiment, the first container is either carried on, or part of, a screen structured for disposal in a urinal.

Certain embodiments include a second container associated at a substantially fixed position in space with respect to the first container. In certain of those embodiments, a quantity of liquid drain cleaner can be disposed inside the second container. Sometimes, the second container is structured to discharge liquid drain cleaner at a substantially constant rate over a period of time in excess of about 14 days subsequent to placing the air freshening device into service. Other times, scented fluid may be carried in a second container that is structured and arranged to discharge scented fluid onto styrene-based material to cause emanation of scent there-from at a substantially constant rate for a period of time in excess of about 14 days subsequent to placing the air freshener device into service. A workable second container may be structured to dispense fluid by way of: rupture of a wall of said second container by a user; or gravity-induced drip from a bulk supply of scented fluid through a small orifice; or osmotic transfer of said scented fluid from a bulk supply; or gas-pump drive of said scented fluid at controlled pressure.

A preferred embodiment includes a support structured for placement inside a urinal and an air freshener carried by the support. A workable air freshener can be structured to operate by way of: emanation of scent from a material selected from the group consisting of (styrene-based polymers and styrene-based rubbers); or gravity-induced drip from a bulk supply of scented fluid through a small orifice; or osmotic transfer of scented fluid from a bulk supply; or gas-pump drive of scented fluid at controlled pressure. Sometimes, a liquid drain cleaner may also be carried by the support. In that case, dispensing structure is desirably configured and arranged to dispense the liquid drain cleaner at a substantially constant rate over a period of time in excess of about 14 days.

The invention can be embodied in a method to manufacture a scent emanator. One such method includes: providing a material selected from the group consisting of (styrene-based polymers and styrene-based rubbers); providing a scented fluid; wetting the material with a quantity of scented fluid to form an emanator having a weight percent of between about 20% and about 200%, where weight percent is calculated as A/B*100, and A is weight of scented fluid and B is weight of material. In general, the styrene-based material is wetted by scented fluid at an ambient temperature of between about 20° C. and about 50° C.; and the scented fluid is placed into contact with the styrene-based material for a period of time greater than about 2 hours. A workable scented fluid is a scent-emitting oil. The method may further include the step of applying the scent-bearing emanator as a coating on a substrate. Sometimes, the emanator material may be placed into a container having openings sized sufficiently small so that the emanator is confined inside the container, but through which openings scent may be dispensed into the environment.

BRIEF DESCRIPTION OF THE DRAWINGS

In the drawings, which illustrate what are currently considered to be the best modes for carrying out the invention:

FIG. 1 is a plan view of an embodiment according to certain principles of the invention;

FIG. 2 is a side view of the embodiment in FIG. 1;

FIG. 3 is a plan view of another embodiment according to certain principles of the invention;

FIG. 4 is a cross-section view of the embodiment in FIG. 3, taken at section 4-4 and looking in the direction of the arrows;

FIG. 7 is a plan view of another embodiment according to certain principles of the invention;

FIG. 8 is a side view of the embodiment in FIG. 7, looking in the direction of the arrows 8-8;

FIG. 9 is a cross-section view of top and bottom portions of a container to accomplish a gravity-assisted release of fluid operable in certain embodiments of the invention;

FIG. 10 is a view in elevation, partially in cross-section of another embodiment according to certain principles of the invention;

FIG. 11 is a view in elevation, partially in cross-section of another embodiment according to certain principles of the invention;

FIG. 12 is a plan view of another embodiment according to certain principles of the invention;

FIG. 13 is a cross-section view of another embodiment according to certain principles of the invention;

FIG. 14 is a cross-section view of another embodiment according to certain principles of the invention;

FIG. 15 is a side view of another embodiment according to certain principles of the invention;

FIG. 16 is a cross-section view of another embodiment according to certain principles of the invention;

DETAILED DESCRIPTION OF THE ILLUSTRATED EMBODIMENTS

Figure 6:
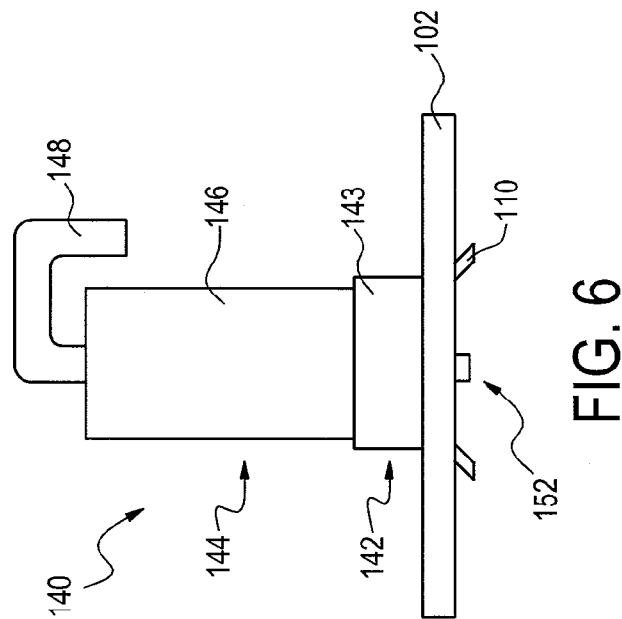
FIG. 6 is a side view of the embodiment in FIG. 5, looking in the direction of the arrows 6-6.

Reference will now be made to the drawings in which the various elements of the illustrated embodiments will be given numerical designations and in which the invention will be discussed so as to enable one skilled in the art to make and use the invention. It is to be understood that the following description is only exemplary of certain principles of the present invention, and should not be viewed as narrowing the claims which follow.

A first embodiment of an air freshener according to certain principles of the invention is illustrated in FIGS. 1 and 2, and generally indicated at 100. Air freshener 100 is particularly adapted for deployment in a urinal. It should be appreciated that alternative embodiments of the invention are not limited to such use. The air freshener 100 and other embodiments described below serve as simple examples to illustrate certain elements.

Air freshener 100 includes a screen 102 substrate, which may be considered a container, or sometimes a support, in that the screen 102 carries a quantity of air fresher material 104. The preferred air freshener material 104 is a scent-bearing styrene-based material manufactured from styrene-based polymers or styrene-based rubbers, as will be described in detail below. One way to obtain the illustrated embodiment 100 is to simply coat the screen 102 with a glue-like mixture of air freshener material 104. Alternatively, it is within contemplation to mold or bond air freshener material 104 onto a substrate 102, or even to form the entire air freshener 100 by molding air freshener material 104 and thereby reduce the number of constituent elements.

A plurality of apertures 106 permit fluid to pass through the air freshener 100, in conventional manner. Typically, the air freshener 100 is placed into a urinal and contacts the bowel around portion(s) of the perimeter 108. Sometimes, one or more optional foot 110, or other operably-shaped protrusion from the screen 102, may be included to better hold the air freshener 100 in a desired position.

An air freshener according to certain principles of the invention, such as air freshener 100, will produce an air freshening scent at a substantially constant level for a period in excess of about 14 days from time of first deployment. In this case, the term "substantially constant level" means that a qualitative standard is employed, and a person in proximity to the device will notice an appreciable odor or scent-emanation from the air freshener 100 for at least about 14 days from first deployment of the air freshener 100 in its use environment. Desirably, the scent will remain at a humanly-perceptible or detectable and operable level for a greater period of time, such as in excess of about 30 days, 60 days, 90 days, or sometimes even longer.

A second embodiment of an air freshener is indicated generally at 120 in FIGS. 3 and 4. A plurality of spokes 122 extend between the rim 124 and an interior wall 126 to define apertures 106. The wall 126, in combination with floor 128, defines a compartment, vessel, or container 130, in which is received a quantity of air freshener material 104. The compartment 130 is structured to permit scent to emanate from the material 104 to the local environment in which the device 120 is deployed. In this embodiment 120, air freshener material 104 may run the gamut from a flowable glue-like substance, to a solid puck or brick-like element, depending on user preference and manufacturing process used to form the air freshening material. Additional details of operable air freshener materials 104 are set forth below, partially in connection with a description of FIGS. 17 and 18. Typically, a portion of perimeter 108 rests against the bowel of the urinal in which the device 120 is deployed. Again, one or more optional foot 110, or other operable extension member, may sometimes be provided to facilitate holding the device 120 in a desired position.

Figure 5:
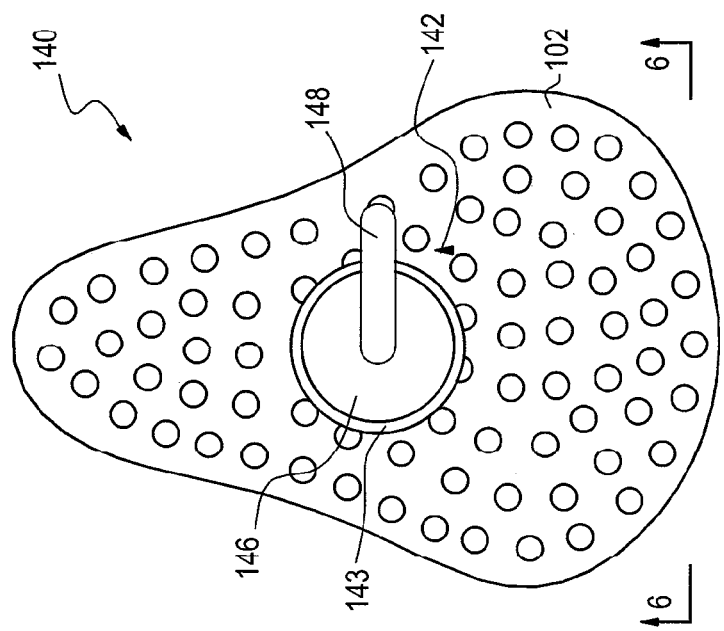
FIG. 5 is a plan view of another embodiment according to certain principles of the invention.

FIGS. 5 and 6 illustrate a third embodiment of an air freshener, generally 140, structured according to certain principles of the invention. Air freshener 140 includes a screen 102 that carries holding structure, generally 142, that is configured and arranged to hold a dispenser of fluid, generally 144, in an operable position. One workable holding structure 142 includes circumscribing wall 143. A currently preferred dispenser of fluid 144 includes the illustrated container 146, which is structured to provide a gravity-assisted, drop-wise release of fluid from a bulk quantity confined inside the container 146. For use as an air freshener, the bulk fluid confined inside container 146 is typically a fragrance of some sort, such as a fragrant oil. In other applications, a bulk fluid sometimes may simply be a volatile oil or other fluid (which may, or may not, be volatile). In one alternative construction that is loosely based upon FIGS. 5 and 6, an air freshening material may be carried on screen 102, and the fluid inside container 146 may be a liquid drain cleaner.

During use in a urinal application, container 146 typically includes a splash guard, such as tube 148, structured to resist fluid flow into the top vent aperture 150 (see also FIG. 9). A workable splash guard may be alternatively structured, including as an umbrella or mushroom providing a shield extending over the vent aperture 150. Container 146 has a discharge end, generally 152, disposed to release fluid through a discharge aperture 154 (see FIG. 9).

An operable dispenser of fluid 144 is capable of releasing fluid at a controlled, substantially constant rate over a period of time in excess of about 14 days, preferably in excess of about 30 day, or so. As used herein, the term "substantially constant rate" means a qualitative standard is employed. In rigorous terms, a quantitative change in flow rate of 20%, 30%, 50%, or even 100% may be considered "substantially constant", depending upon the application For air-freshening purpose, the more important effect is accomplishing a humanly-perceptible substantially constant air freshening smell. In application as a drain cleaner, the important effect is accomplishing reliable release of sufficient fluid to maintain drain cleanliness over the desired time increment.

One workable fluid dispenser 144 operates under principles of gravity-induced drip from a bulk supply of fluid through a small orifice. Certain details of construction and operation of such a dispenser 144 are disclosed in U.S. Provisional patent application No. 62/164,650. A second workable fluid dispenser 144 operates under principles of osmotic transfer of fluid from a bulk supply. Certain details of construction and operation of that type of dispenser 144 are set forth in U.S. Pat. No. 8,240,261. A third workable fluid dispenser 144 operates under principles of gas-cell drive of fluid at substantially controlled pressure. Certain details of construction and operation of that third type of dispenser 144 are set forth in U.S. Pat. Nos. 6,823,383; 6,957,779; and 8,939,435. The entire disclosures of the patent documents mentioned in this paragraph are hereby incorporated as though set forth herein in their entirety.

FIGS. 7 through 9 illustrate certain details of construction of a fourth 'type' of embodiment, generally indicated at 170, structured according to certain principles of the invention. The illustrated embodiment 170 includes two fluid dispensers 144 carried on a support or screen 102. In the particular embodiment illustrated in FIGS. 1 and 8, the fluid dispensers 144 are of the gravity-induced drip type 146. One container 146 is typically used to dispense fragrance, and the other container 146 is typically used to dispense drain cleaner. Other types of fluid dispensers 144 may be employed, and may be combined in more than one type and number. It is also within alternative contemplation that a quantity of styrene-based fragrance may be used as the air fresher element, and one or more fluid dispenser 144 may be employed to dispense fluid drain cleaner or other fluid. In the latter case, fragrant material 104 may be applied as a coating to the screen 102, may form the screen/support 102, or may be confined in a compartment, such as a container 130 (FIG. 4) formed by a wall 126 or 143 associated with a screen or support 102.

The embodiment in FIG. 10, and generally indicated at 180, illustrates an alternative type of air freshener. Air freshener 180 includes a fluid dispenser, generally 144, adapted to discharge fluid onto an emanator 182. A currently preferred emanator 182 is formed from, or includes, a styrene-based polymer or a styrene-based rubber, and the fluid dispenser 144 discharges a fragrant oil onto the emanator 182.

One workable fluid dispenser 144 includes the illustrated gravity-induced drop type 146. In that case, some sort of seals are desirably provided to confine fluid inside the container 146, e.g. during shipping and handling prior to placing the device 180 into service. A workable seal includes the illustrated ubiquitous tear-off foil cover 184 that is removably bonded to the container 146 and blocks fluid flow from respective vent or discharge openings. Other conventional sealing structures may be used, including stoppers, corks, twist-off threaded caps, and the like. Sometimes, suspension structure, such as a handle or bail 186 may be provided to facilitate placement of a device into operable service as a suspended element. Alternatively, some sort of stand-up support structure, such as a foot (not illustrated), may permit placement of a device 180 in an operable orientation onto a supporting surface, such as a table or the floor.

FIG. 11 illustrates another embodiment of an air freshener, generally 190, that is structured for operation over an extended period of time. An emanator 182 defines at least part of a volume 192, in which an excess quantity of fragrant fluid 194 is stored. A currently preferred emanator 182 includes a material selected from, or includes, a styrene-based polymer or a styrene-based rubber, and the fluid 194 (typically a fragrant oil) is disposed in direct contact with the emanator 182. A cover or cap 196 may be sealed against undesired fluid flow through a fill-opening by a seal element 184.

FIG. 12 illustrates an embodiment, generally 200, that is structured to provide an enlarged surface area 202 to provide a more concentrated source of scent over a significant period of time. The emanator of embodiment 200 is formed from a coiled tube with a wall made from a styrene-based polymer or a styrene-based rubber. Similar to embodiment 190, fragrance fluid is disposed in direct contact with the styrene-based material, and may be confined by one or more seal element 184.

The embodiment, generally 210, illustrated in FIG. 13 represents the case where a pocket or space is formed between two layers of plastic- or rubber-like materials. At least one side of a pocket or void includes styrene-based material. That is, one or both of top sheet 212 or bottom sheet 214 is a styrene-based material. Fragrant fluid 194 is placed into the void, pocket, or compartment 216 that is formed between top sheet 212 and bottom sheet 214, and the edges surrounding the void 216 may be sealed. Alternatively, the fragrant fluid may be injected into the void 216.

FIG. 14 illustrates an embodiment, generally 220, including a separate and impermeable pouch 222 in which fragrant fluid 194 is initially confined. Again, one or both of top sheet 212 or bottom sheet 214 is typically formed from a styrene-based material. However, a workable sheet 212, 214 can be manufactured from other materials, including styrene-based polymers, styrene-based rubbers, EPDM, gum rubber, cellulosic rubber, and other materials that absorb and emanate a fragrant material. A workable pouch can be made from plastic, or plastic-like materials that are impermeable to the fragrant fluid 194. A user may rupture the pouch 222 to release fluid into contact with the styrene-based material. That material then operates as an emanator to disperse scent into the environment local to the device 220. A pouch 222 may be ruptured by stepping on the device 220, poking the pouch 222 with a sharp object (desirably making a hole in sheet 212 or 214 too small to leak), or otherwise causing a break in the wall of the pouch 222 through which fluid 194 may escape for contact with the styrene-based material.

FIG. 15 illustrates a generalized object made from a styrene-based material, generally indicated at 230. The object 230 can be any sort of 3-dimensional shape. The object 230 is soaked in, or otherwise wetted by, fragrant fluid at a temperature between about 20° C. and about 50° C. for a period of time greater than about 2 hours to form an emanator 232. In such a process, scented fluid is dispersed into the material to a weight percent of between about 20% and about 200%, where weight percent is calculated as A/B*100, and A is weight of scented fluid and B is weight of material. In a preferred embodiment, the weight gain of a styrene-based rubber-like material is about 35%.

For example, the device 230 in FIG. 15 can be a flat section of styrene-based polymer or styrene-based rubber seen in side view. The plan view can be formed to resemble a shape, such as a pine tree. A logical fragrant or scented fluid for that case would include pine-scented fragrant oil. Provision may be made to permit suspending the device 230 from, for non-limiting examples: a rear view mirror in an automobile; or a clothes-rod in a closet.

FIG. 16 illustrates a generalized embodiment, generally 240, of a multi-compartment fluid dispenser. Device 240 can be manufactured by bonding top sheet 242 to bottom sheet 244 around perimeters of void compartments, similar to the embodiments in FIGS. 13 and 14. Multiple compartments can be made, similar to bubble wrap. The illustrated embodiment 240 includes two compartments, namely compartment 246 and compartment 248. Top and bottom sheets 242, 244 may conveniently be manufactured from polymer sheets, including plastic, rubber, and plastic-like materials. It is not necessary (but not precluded, either), that either or both of sheets 242, 244 be a styrene-based material.

In an exemplary device 240 that is structured as a combination urinal air freshener and drain cleaner, a first fluid 250 (which is a fragrant fluid) is inserted into void 246 by way of first and second puncture holes generally indicated at 252. One puncture hole may admit fluid 250 into the void or cavity 246, while the second puncture hole may release any entrapped air from cavity 246. A seal element, such as a peel-off removable foil cap 184, can then be installed to entrap the fluid 250 during, for example, transportation and handling prior to deployment of that device 240. Similarly, a drain cleaning fluid 254 can be placed into cavity 248. One operable drain cleaning fluid includes tetra sodium ethaline diamine tetracetic acid tetra sodium salt ($C_{10}H_{12}Tv_2O_8Na_4$) or tetra sodium EDTA. Desirably, the puncture holes 252 are sized to operate as discharge orifices permitting a gravity-induced discharge of respective fluid over a desired extended period of time. If required, one or more vent hole may be formed in a sheet opposite to the discharge aperture. Certain embodiments may be self-pressurized to urge fluid flow from a cavity.

Figure 17:
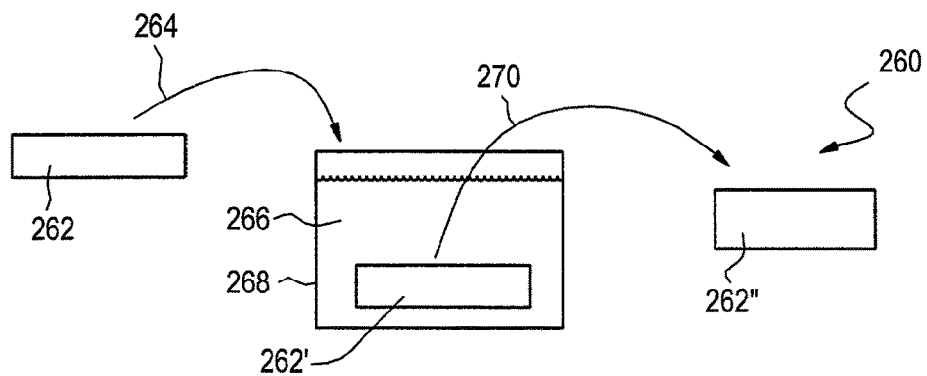
FIG. 17 is a cartoon illustrating operable steps of manufacture of an air freshening material according to certain principles of the invention.

FIG. 17 illustrates one process, generally 260, operable to create an emanator according to certain principles of the invention. One or more piece of styrene-based material 262 is placed into contact (indicated at arrow 264) with a fragrant fluid, such as fragrant oil 266. As illustrated, the contact can be simple submersion in a container 268, where the material 262' absorbs the fragrant fluid. Desirably, the fluid is maintained at a temperature of between about 20° C. and about 50° C. for a period of time greater than about 2 hours, preferably about 24 hours. The material may then be removed from the fluid, as indicated at arrow 270, resulting in emanator 262". Emanator 262" may be used in an exemplary embodiment 240, such as illustrated in FIG. 15.

Figure 18:
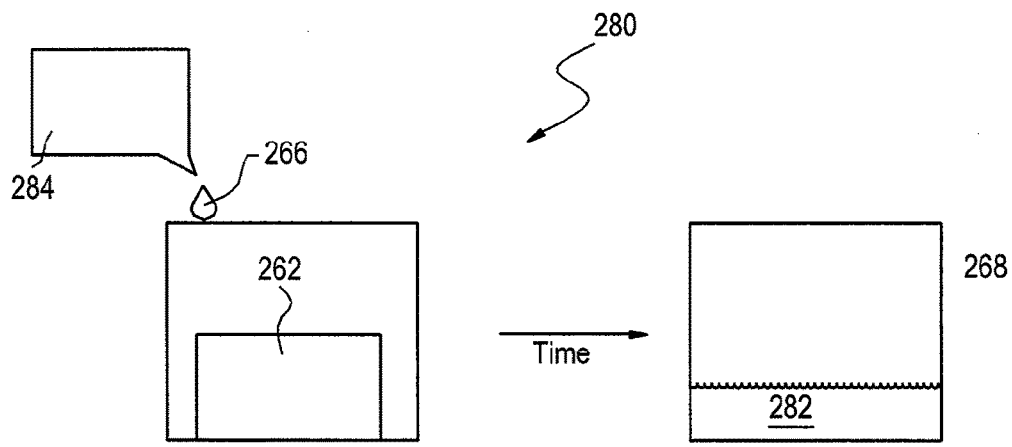
FIG. 18 is a cartoon illustrating operable steps of manufacture of another air freshening material according to certain principles of the invention.

FIG. 18 illustrates a second process, generally 280, operable to form an alternative emanator material 282. A sufficient quantity of fragrant oil is poured from a container 284 onto one or more piece of styrene-based material 262 in a second container 268. After a period of time, and in an ambient fluid temperature between about 25° C. and about 50° C. for a period of time greater than about four hours, the material 262 absorbs a sufficient amount of oil as to change viscosity from a solid to a thick and viscous material. The resulting material 282 may be characterized as a scent-emitting glue-like substance, and is very sticky. The glue-like material 282 may then conveniently be applied as a coating to a substrate, such as screen 102 illustrated in FIG. 1, to form an air fresher. Viscosity of the glue-like material is a function of the amount of fragrance absorbed by the base rubber, or rubber-like, material.

It has been determined by experimentation that only certain rubber, or rubber-like, compositions absorb and release fragrant oil under substantially ambient conditions (e.g. between about 25° C. and about 50° C.). Effective and operable rubber compounds include styrene-based EPDM, natural rubbers, gum rubbers, and cellulosic rubbers.

Figure 19:
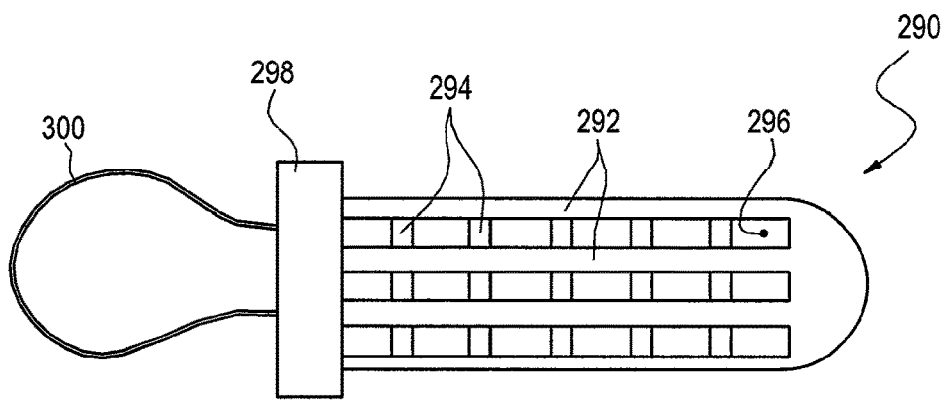
FIG. 19 is a side view of a container in which air freshening material structured according to certain principles of the invention may be placed.

A workable emanator-holding device is illustrated generally at 290 in FIG. 19. Device 290 may be characterized as a thimble, having an internal volume defined by axially extending ribs 292 and circumferentially circumscribing bands 294. Together, the ribs 292 and bands 294 form a plurality of apertures 296. A quantity of emanator material, such as 262" or 282, is placed into the internal volume of container 290, and a cap 298 may be installed to confine the material in place. Desirably, the apertures 296 are sized sufficiently small as to resist escape of a fluid-like material 282. Provision, such as a loop 300, may be included to facilitate suspending device 290 in use as an air freshener. A device 290 may be embodied for direct contact with clothes in a clothes drier, thereby imparting a fresh scent to drying clothes.

EXAMPLE 1

A piece of styrene-butadiene rubber (SBR) weighing 6.198 grams was dipped into a sufficient quantity of citrus fragrance oil as to be fully submerged. After 12 hours at about 30° C., the SBR piece was removed, dried by paper towels, and weighed. The resulting weight was 14.688 grams. Therefore, the total weight gain was 8.49 grams. That constitutes a weight gain of over 100% at about 30° C. Then, the piece of SBR was placed into a bathroom having an approximately 120 ft$^2$ floor, and the citrus smell filled the room and was very strong. The strong citrus smell persisted for more than 30 days (as of the time this Specification was drafted).

EXAMPLE 2

Another sheet of SBR rubber sheet was pierced by a sharp knife at several places to promote an increase in surface area. The perforated rubber sheet was then dipped into fragrance. After about 24 hours in an approximately 35° C. environment, the sheet absorbed more than 75% of its weight in fragrance.

It has been observed that the styrene portion of styrene-based materials can absorb fragrant oil and form a glue-like substance when exposed to liquid scented oil at a temperature between about 25° C. and about 50° C. A trigger event that appears to cause the phase transition between a solid polymer and a glue-like material is addition to the polymer of about 50% (by weight) of fragrance. Preferably, about 75% to 150% of the weight of the styrene-based material will be absorbed during the process to transform a solid polymer into a glue-like fragrant material.

It has also been observed that EPDM and Natural Gum rubbers may also absorb more than about 50% of their weight in fragrant oil, simply by submersion in fragrant oil at substantially ambient temperature for a sufficient length of time. Furthermore, cellulosic rubbers have been observed to operate in a similar manner.

EXAMPLE 3

In one experiment, 1 g of polystyrene foam obtained from a crushed-up foam coffee cup was placed in a polypropylene cup. 1 g of fragrance was added to the polypropylene cup to bathe the crushed-up foam polystyrene. The fragrance was totally absorbed for a 100% weight gain. Although stirring was not part of the procedure, a viscosity change was detected at an estimated 75% weight gain. After about 4 hours, a fragrant glue was formed from the combination. The fragrant glue was very sticky, and would stick to any surface, especially porous surfaces like paper, cloth, etc. Furthermore, the fragrant glue appears to emit fragrance at a controlled rate. The fragrant glue-like substance was viscous, and would slowly extend in a drip-like extension from a stirring stick used to pick up the mixture. The thusly-formed fragrant glue was placed in a central container of an air freshener device, such as container 130 in FIGS. 3 and 4; the air freshener device was placed in the sink of the aforementioned bathroom; and fragrance level in the bathroom was monitored. The fragrance level was humanly appreciable and relatively constant for a period of time in excess of 18 days.

It has been observed that after losing 20-30% of the fragrance, the "stickiness" decreased. The resulting material then possessed a tacky property similar to a "post-it" note, or glue used to affix a removable object to a substrate. The object can then be removed without retaining residual adhesive, or the adhesive may be easily removed.

Figure 20:
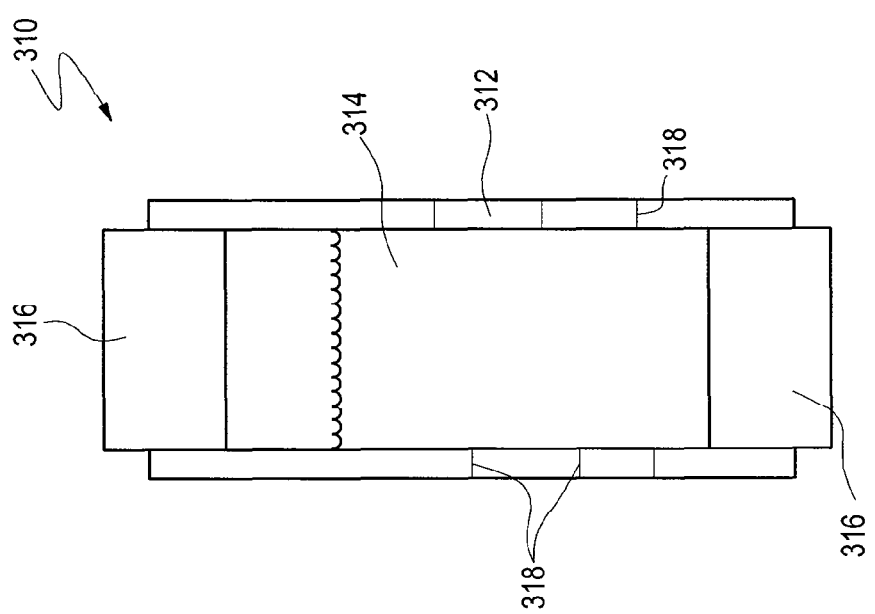
FIG. 20 is a cross-section view in elevation of another embodiment.

The embodiment generally indicated at 310 in FIG. 20 includes an EPDM rubber tube 312, in which may be confined a fragrance or other fluid 314. Tube 312 is capped on its open ends by polypropylene stoppers 316 to resist undesired loss of fluid 314. A plurality of through-thickness punctures or piercings 318 can be created by piercing the tube 312 with a sharp knife. Punctures 318 inherently form very small apertures through which fragrance or other fluids may slowly diffuse to the outer surface for evaporation there-on, or dripping there-from. That is, rubber, and rubber-like materials tend to self-heal to form very small apertures that can permit a slow migration of fluid, or even substantially or completely resist fluid flow. Punctures 318 may also increase the effective surface area of the tube 312. In this kind of punctured embodiment, virtually any sort of rubber, or rubber-like compound, and even some plastic, or plastic-like materials, may be workable.

Figure 21:
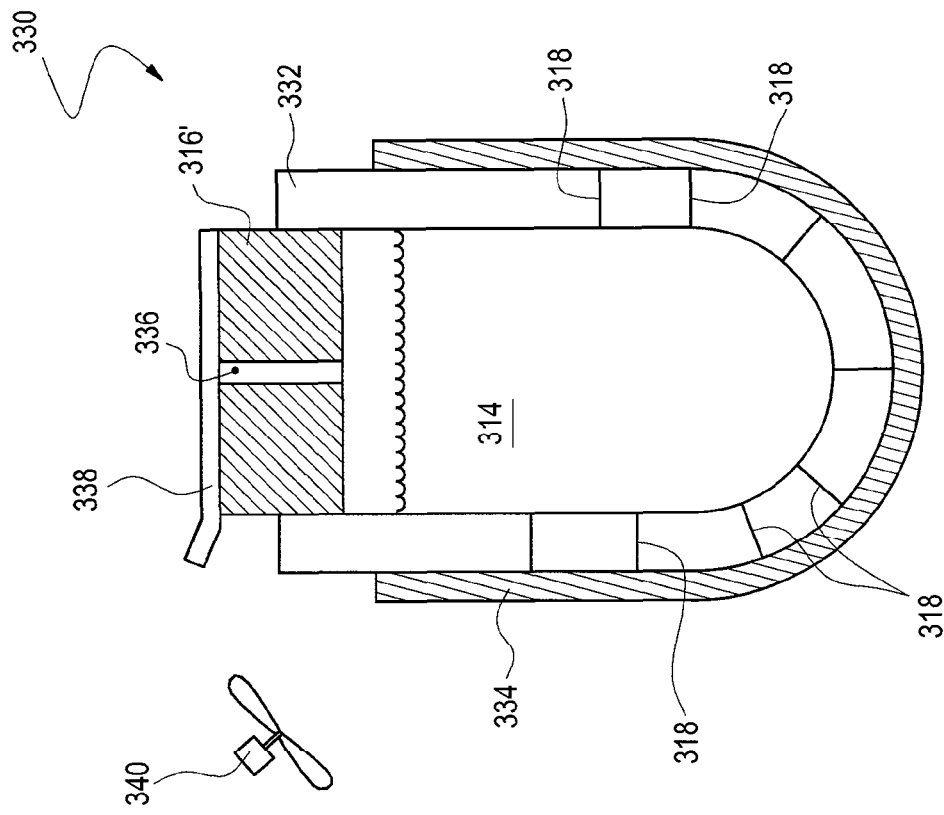
FIG. 21 is a cross-section view in elevation of another embodiment.

For example, the embodiment illustrated in FIG. 21 and generally indicated at 330 includes a container 332 pierced by a plurality of punctures 318. Container 332 may be formed from virtually any rubber, or rubber-like compound, and even some plastic, or plastic-like materials. Bulk fluid 314 migrates through the slits 318 and is dispersed by emanator 334. A workable emanator may be made from paper, or other material that can absorb and disperse fluid for evaporation from an external surface. A stopper 316' includes a fill-aperture 336 that is capped by foil wrapper 338 to resist undesired fluid escape. A fan 340 may sometimes be included to assist in dispersing scent into the environment in which the device 330 is placed into service. In fact, such a fan 340 may be included in any embodiment of the invention, as desired.

Figure 22:
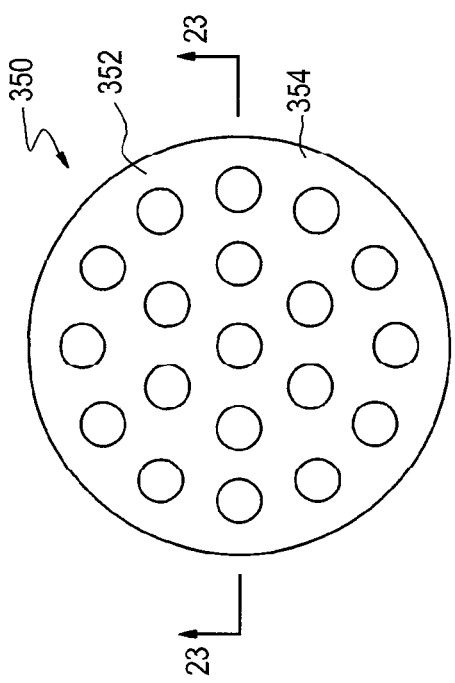
FIG. 22 is a top, or plan view of an embodiment structured similar to bubble wrap, and containing fragrance inside a plurality of bubbles.
Figure 23:
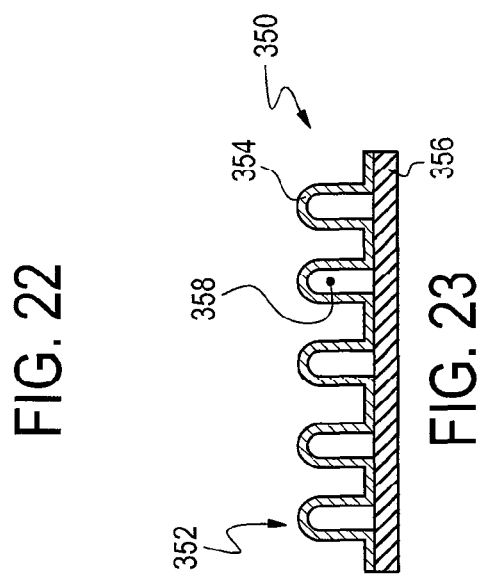
FIG. 23 is a side view of the embodiment in FIG. 22, taken at section 23-23 and looking in the direction of the arrows.

Another embodiment is illustrated in FIGS. 22 and 23, and generally indicated at 350. Embodiment 350 is somewhat analogous to bubble wrap that is used to protect items during shipping. Bubbles, one of which is generally indicated at 352, are formed between top sheet 354 and substrate 356. A beneficial fluid may be loaded into the interior 358 of a plurality of bubbles. Either, or both, of top sheet 354 and substrate 356 may be formed from a rubber or polymer to form an emanator. Beneficial fluids encompass fragrant oils, mosquito repellant, drain cleaners, and the like. The illustrated embodiment 350 is structured to release the bulk fluids at a slow and controlled rate into the environment in which embodiment 350 is placed into service.

Figure 24:
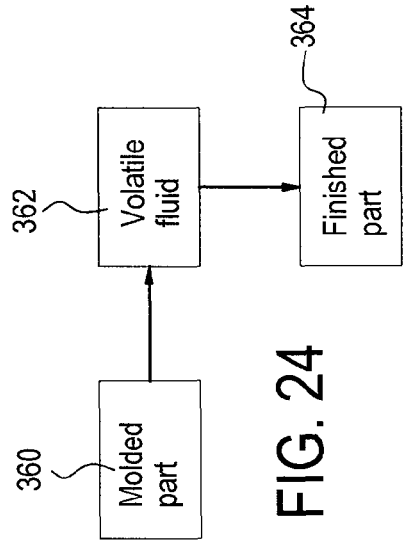
FIG. 24 is a process chart for making one type of embodiment according to ceratin principles of the invention.

An air freshener according to certain principles of the invention may be very simply manufactured. As illustrated in FIG. 24, an item may be molded or otherwise manufactured from a workable absorbant/releasant material, such as the various rubbers described above. The item is provided in substantially final form as indicated in box 360. Then, the item is placed into contact with a quantity of volatile fluid, as indicated in box 362. The fluid is absorbed into the item at substantially ambient conditions (e.g. between about 25° C. and about 50° C.). Time of contact by fluid can be controlled to cause a desired amount of fluid uptake by the item. The result becomes a finished item, ready for service, as indicated in box 364.

EXAMPLE 4

An embodiment structured according to FIG. 20 was made from a 2 inch length of about 1 inch diameter EPDM tube having a wall thickness of about 1 mm. Several piercings were made in the lower portion of the tube using a sharp knife. A polypropylene stopper was inserted into the bottom, and the tube was half-filled with fragrance. The tube was then sealed with a top polypropylene stopper, and the assembly was placed into an open container. The container was placed into a small bathroom, where the fragrance emanation has remained humanly detectable at a strong level for over 28 days. The fragrance level remains strong as of the time this document is being drafted.

The terms "fragrance" and "fragrant oil", and the like are employed as a convenience in this disclosure to characterize bulk fluids. These terms are intended to encompass any volatile or beneficial fluid or agent, irrespective of any scent characteristic of the fluid. Beneficial agents include volatile and non-volatile fluids that are beneficial for the environment surrounding the emanation of such fluids. Exemplary beneficial agents nonexclusively include mosquito repellant, citric oils, cleaners, deodorizers, moisturizing liquids, and the like.

Exemplary materials for use as an absorber/releaser or emanator in certain embodiment of the invention include styrene-based polymers such as: acrylonitrile-butadiene-styrene (ABS), styrene-butadiene-styrene (SBS), styrene-acrylonitrile (SAN), styrene-isoprene-styrene (SIS), styrene-ethylene-butadiene-styrene (SEBS), styrene-ethylene-propylene-styrene (SEPS), and combinations thereof; and operable styrene-based rubbers non-exclusively include: styrene-butadiene-rubber. As previously mentioned, EPDM, Natural rubbers, and cellulosic rubbers are also operable, among other workable compositions.

Also, as previously indicated, certain embodiments are operable even if the base material used to confine a bulk fluid does not significantly absorb and subsequently release the bulk fluid (i.e. a fragrance, volatile oil, or other beneficial fluid) at approximately ambient temperatures on the planet Earth. For example, no significant fragrant oil uptake was observed for Silicone rubber, polypropylene, polyethylene, acrylic rubbers, PVC, EVA at approximately room temperature (about 20° C.). However, embodiments structured according to certain principles of the invention may encompass a bulk fluid container made from, or including, one or more of such materials.

Figure 25:
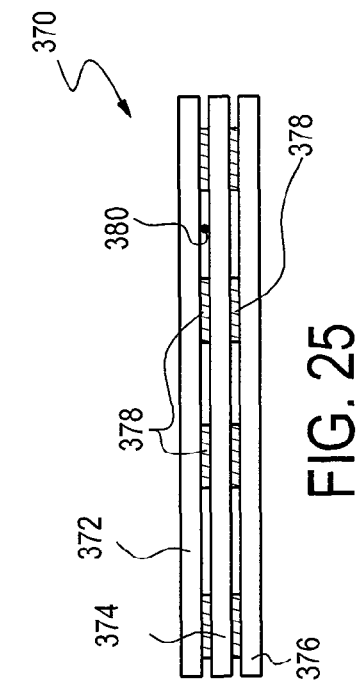
FIG. 25 is a side view in perspective of a portion of an air freshener including micro-channel structure according to certain principles of the invention.

A workable embodiment may include an emanator that can be structured to include microporous or nanoporous elements. Further, a workable emanator can include microchannels. A workable emanator can be thought of as a sponge, and structured accordingly. For example, FIG. 25 illustrates a portion of a microchannel emanator. The illustrated emanator, generally indicated at 370, is formed by a series of stacked and bonded-together sheets and spacers. Any number of sheets and spacers may be employed, as desired. A small sample is illustrated for convenience. Top sheet 272, middle sheet 274, and bottom sheet 276 form top and bottom surfaces for contact with fragrance fluids. A plurality of spacers 378 form sides, or walls, of a plurality of microchannels 380, in which to receive a fragrant fluid. The fragrance can be injected into, or aspired subsequent to evacuation of air from, the channels 380.

Preferably, the sheets 272, 274, and 276 are formed from a material that absorbs and subsequently emanates fragrance. However, certain alternative embodiments may rely only upon evaporation or emanation of scent from the open ends of the microchannels 380. Microchannels can be sized in any workable range operable to maintain capillary attraction to the fragrant fluid employed in a device. For non-limiting example, channel height can be between 10 and 100 µm; channel width can be 10 to 500 µm; and sheets can be 50 to 200 µm thick, or so.

Figure 26:
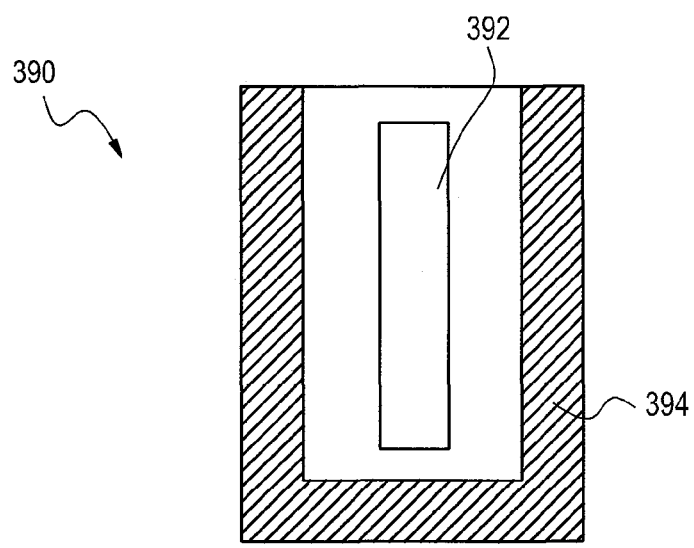
FIG. 26 is a side view, in cross-section, of another embodiment structured according to certain principles of the invention.

It is within contemplation that certain embodiments may include a heating element to facilitate, or accelerate, emanation of fragrance. For example, FIG. 26 illustrates a heated embodiment, generally indicated at 390, which includes an emanator 392 that is warmed by a heating element 394. An operable heating element 394 may be battery operated, or obtain electrical energy by a conventional cord-and-outlet arrangement. A workable emanator 392 may be structured according to any of the above-described embodiments.

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus, comprising:
a first container; and
an air freshener disposed in association with said first container; wherein
said air freshener comprises an emanator formed from a rubber material selected from the group consisting of styrene-based rubber, gum rubber, and cellulosic rubber; and
a scented fluid dispersed into said rubber material; wherein
said emanator comprises a unitary emanator surface area structured to change in size responsive only to uptake or emanation of volatile fluid.

2. The apparatus according to claim 1, wherein:
a portion of said first container is formed from said rubber material.

3. The apparatus according to claim 2, wherein:
an excess quantity of said scented fluid in a fluid state is carried inside said first container, and said first container functions as an emanator to disperse scent from said excess quantity of fluid into the environment.

4. The apparatus according to claim 2, wherein:
said scented fluid in a liquid state is also carried in a second container that is structured and arranged to discharge said scented fluid from said second container onto said rubber material to cause emanation of scent there-from at a substantially constant rate for a period of time in excess of about 14 days subsequent to placing said apparatus into service.

5. The apparatus according to claim 4, wherein:
said second container is structured and arranged to dispense fluid onto said rubber material by way of:
rupture of a wall of said second container by a user; or
gravity-induced drip from a bulk supply of scented fluid through a small orifice; or
osmotic transfer of said scented fluid from a bulk supply; or
gas-pump drive of said scented fluid at controlled pressure.

6. The apparatus according to claim 1, wherein:
said air freshener is disposed inside said first container.

7. The apparatus according to claim 1, wherein:
said air freshener is carried as a coating on said first container.

8. The apparatus according to claim 1, wherein:
said first container is either carried on, or part of, a screen structured for disposal in a urinal.

9. The apparatus according to claim 8, further comprising:
a second container associated at a substantially fixed position in space with respect to said first container; and a quantity of liquid drain cleaner disposed inside said second container; wherein said second container is structured to discharge said liquid drain cleaner at a substantially constant rate over a period of time in excess of about 14 days subsequent to placing said apparatus into service.

10. The apparatus according to claim 1, wherein:

said scented fluid is a scent-emitting oil.

11. The apparatus according to claim 1, wherein:

said scented fluid is disp/ersed into said rubber material to a weight percent of up to about 200%, where weight percent is calculated as A/B*100, and A is weight of said scented fluid and B is weight of said rubber material.

12. The apparatus according to claim 11, wherein:

said scented fluid is dispersed into said rubber material to a weight percent of between about 30% and about 150%.

13. The apparatus according to claim 1, wherein:

said styrene-based rubbers comprises:

styrene-butadiene-rubber.

14. An apparatus, comprising:

a support structured for placement inside a urinal; and an air freshener associated with said support; wherein:

said air freshener is structured to operate by way of:

emanation of scent from a rubber material, the rubber material comprising styrene-based rubber and being structured to provide a unitary emanating surface area that changes in size only due to uptake or emanation of volatile fluid during the entire operable service life of said air freshener.

15. The apparatus according to claim 14, further comprising:

a liquid drain cleaner carried by said support; and dispensing structure configured and arranged to dispense said liquid drain cleaner at a substantially constant rate over a period of time in excess of about 14 days.

16. A method, comprising:

providing a pre-formed emanator substrate manufactured by injection-molding to form an air freshener comprising a unitary emanator surface area structured to change in size only due to uptake or emanation of a scented fluid during the entire useful life of a resulting emanator, said substrate comprising a material selected from the group consisting of styrene-based rubber, gum rubber, and cellulosic rubber;

providing said scented fluid;

wetting said substrate with a quantity of said scented fluid to form said emanator having a weight percent of less than about 200%, where weight percent is calculated as A/B*100, and A is weight of said scented fluid and B is weight of said material.

17. The method according to claim 16, wherein:

said substrate is wetted by said scented fluid at an ambient temperature of between about 20° C. and about 50° C.; and said scented fluid is placed into contact with said substrate for a period of time greater than about 2 hours.

18. The method according to claim 16, wherein:

said scented fluid is a scent-emitting oil.

19. The method according to claim 16, further comprising:

applying said emanator as a coating on a substrate.

20. The method according to claim 16, further comprising:

placing said emanator into a container having openings sized sufficiently small so that said emanator is confined inside said container, but through which openings scent may be dispensed into the environment.

* * * * *